United States Patent [19]
de Leeuw

[11] 4,012,200
[45] Mar. 15, 1977

[54] APPARATUS FOR REMOVING LIQUID FROM THE INSIDE OF A TEST TUBE

[75] Inventor: Jan de Leeuw, Akersberga, Sweden

[73] Assignee: AutoChem Instrument Aktiebolag, Bromma, Sweden

[22] Filed: Feb. 12, 1976

[21] Appl. No.: 657,690

[30] Foreign Application Priority Data

Feb. 24, 1975 Sweden .......................... 7502005

[52] U.S. Cl. .................. 23/259; 134/21; 134/22 C; 23/292
[51] Int. Cl.[2] .................. B01L 11/00; B08B 5/04; B08B 9/00
[58] Field of Search ............... 23/259, 292; 134/21, 134/22 R, 22 C, 23, 24, 37; 15/316 R, 406

[56] References Cited
UNITED STATES PATENTS

| | | | |
|---|---|---|---|
| 2,259,367 | 10/1941 | Ely et al. | 15/406 X |
| 3,572,998 | 3/1971 | Anthon | 23/259 |
| 3,836,329 | 9/1974 | Jordan | 23/259 X |

Primary Examiner—Joseph Scovronek
Attorney, Agent, or Firm—George H. Mitchell, Jr.

[57] ABSTRACT

A device for removing liquid from a test tube consists of an evacuation tube having a flexible plate extending outwardly from its lower end, the plate having a number of radial grooves connected at the center, so that by pressing the bottom of the test tube against the flexible plate, moisture can be removed by suction applied to the evacuation tube.

3 Claims, 3 Drawing Figures

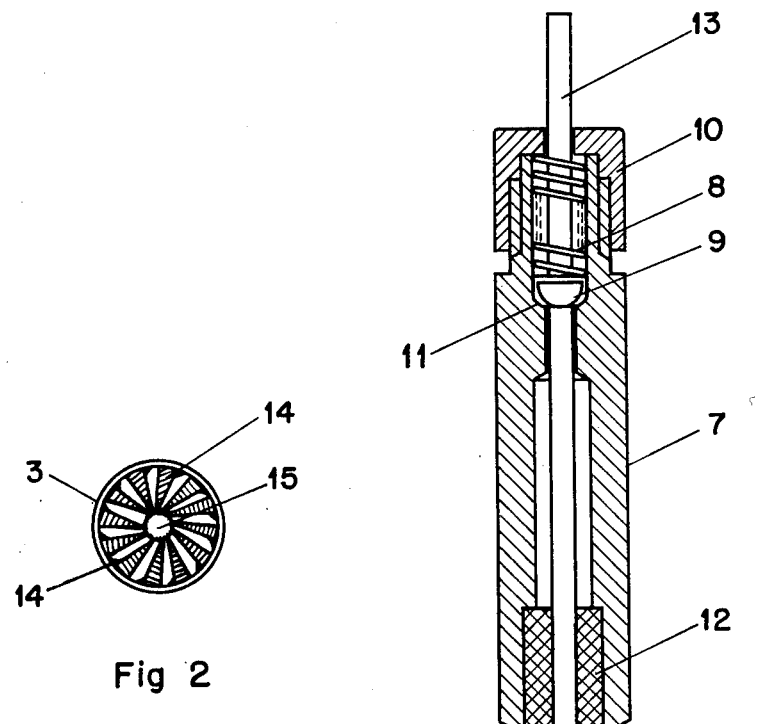
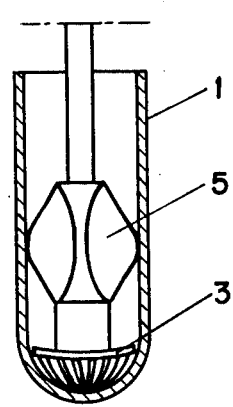
Fig 2
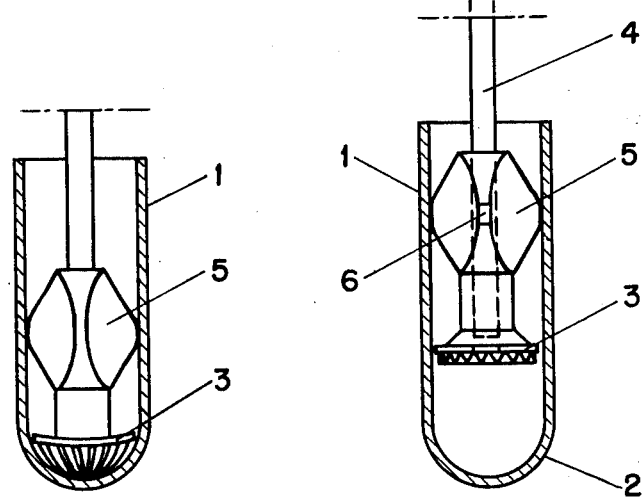
Fig 3  Fig 1

APPARATUS FOR REMOVING LIQUID FROM THE INSIDE OF A TEST TUBE

The present invention refers to an apparatus for removing liquid from the inside of a test tube, the apparatus comprising an evacuation tube connected to a vacuum source and means connected to the evacuation tube which has a diameter bigger than the outer diameter of the evacuation tube.

In order to remove liquid from the inside of a test tube it is known per se to have an evacuation tube which at its end is provided with a sphere having a diameter slightly below the inner diameter of the test tube. However, with such a device it is not possible to obtain a complete removal of liquid from the test tube. Thus when the sphere is brought down to the bottom of the test tube, a slot between the sphere and the test tube will be formed either at the cylindrical inner surface of the test tube or at the centre of the bottom of the test tube since it is almost impossible to give the sphere the same shape as the bottom of the test tube. Furthermore the evacuation of liquid is decreased when the sphere reaches the bottom of the test tube. It is an object of the present invention to provide a complete removal of liquid from the inside of a test tube, the characteristics of the invention appearing from the enclosed claims.

The apparatus according to the invention will now be described in detail reference being made to the enclosed drawing in which:

FIG. 1 is a cross-sectional view of the device according to the invention;

FIG. 2 shows a plate included in the apparatus seen from below and

FIG. 3 shows the device in a position where the plate is pressed against the bottom of the test tube.

In FIG. 1 reference 1 denotes a test tube from which liquid on the walls is to be removed. The test tube is provided with a spherical bottom 2. The liquid removing device comprises a plate 3 of an elastic material such as soft plastics or rubber. It has a diameter which is slightly below the inner diameter of the test tube 1. The plate 3 is attached to a tube 4 which also carries a centering device 5. The centering device is provided with a number of protrusions having a radial extension so that surfaces 6 of the protrusions are brought in contact with the inside of the test tube 1 when the device is introduced into the test tube. By means of this centering means a slot of uniform width will be obtained between the plate 3 and the inside of the test tube 1.

The tube 4 is axially displaceable in a socket 7 and is subject to pressure from a pressure spring 8 which is tensioned between a flange 9 attached to the tube 4 and a cap 10 screwed on the socket 7. By means of the spring 8 the flange 9 is pressed towards a stop 11 in the socket 7, but when the plate 3 is subject to pressure for instance from the bottom surface 2 of a test tube 1, the tube 4 can be moved upwards with respect to the socket 7 whereby the tube 4 slides into a guiding device 12 of the socket 7. The guiding device 12 is suitably made from a soft material such as foam rubber and furthermore the flange 9 is semispherical. With this design it is possible for the plate 3 and the centering device 5 to be moved radially and they could thus be introduced in a test tube even if the tube is not exactly coaxially positioned with the tube 4. A part 13 protruding through the cap 10 is to be connected with a vacuum chamber or a similar means for generating an underpressure.

As appears from FIG. 2 the plate 3 is on its lower side provided with a number of radial grooves 14 which run from the periphery of the plate towards its centre. In its centre the plate is furthermore provided with a bore 15 which is connected to the tube 4 and thus with the above mentioned vacuum chamber.

When a test tube is brought up against the above described device and air is sucked through the tube 4 an intensive air stream will flow downwards in the test tube and will pass the edge of the plate 3 through the narrow slot between the plate and the inner wall of the test tube 1. Thereby, drops of liquid or other moisture, located on the inner wall of the test tube will be brought down towards the spherical bottom 2 of the test tube. When finally the bottom of the test tube reaches the plate 3 the plate will be shaped so that it comes in contact with the bottom as described in FIG. 3. By means of the spring 8 it is thereby ascertained that the plate 3 reaches the bottom and is shaped along the bottom even if test tubes of different heights are applied to the apparatus.

In its lower position the plate 3 will come in contact with the bottom of the test tube 1, whereby the grooves 14 together with the bottom 2 of the test tube will form channels connected to the tube 4. Through these channels one will obtain an intensive air stream which effectively brings any moisture of the tube 1 out of the test tube and thus the test tube will be completely dry.

In the above description it has been assumed that the test tube is brought up against the liquid removing device but obviously this device could also be brought down towards the test tube until the plate 3 reaches the bottom and gets its semispherical shape. Furthermore the centering means 5 could be provided with an arbitrary number of protrusions and the plate 3 could of course on its lower side be provided with a desired number of grooves.

We claim:

1. Apparatus for removing liquid from the inside of a test tube, the apparatus comprising an evacuation tube connected to a vaccum source and means connected to the evacuation tube having a diameter greater than the outer diameter of the evacuation tube, characterized in that said means is constituted by an elastic plate arranged at the end of the tube, the plate having a diameter slightly smaller than the inner diameter of the test tube, a centering means arranged on the evacuation tube to provide a uniform annular slot between the plate and the inner wall of the test tube, the lower side of the plate being provided with radial grooves, the elasticity of the plate being such that when pressed against the bottom of a test tube the grooves and the bottom of the test tube will form channels in communication with the evacuation tube.

2. Apparatus according to claim 1, characterized in that said apparatus includes a holder and a compression spring within the holder, the evacuation tube being longitudinally displaceably received within the holder, the spring being connected between the holder and the evacuation tube to urge displacement of the tube in one direction.

3. Apparatus according to claim 2, characterized in that the evacuation tube is provided with a semi-spherical flange in contact with the spring, the upper part of the holder including a stop against which said flange abuts to limit said displacement of the evacuation tube, the lower part of the holder containing a resilient guiding device for the evacuation tube.

* * * * *